(12) United States Patent
Messenger

(10) Patent No.: US 7,135,603 B2
(45) Date of Patent: Nov. 14, 2006

(54) PROCESS FOR THE PRODUCTION OF OLEFINS

(75) Inventor: Brian Edward Messenger, Englefield Green (GB)

(73) Assignee: Innovene Europe Limited, Middlesex (GB)

(*) Notice: Subject to any disclaimer, the term of this patent is extended or adjusted under 35 U.S.C. 154(b) by 492 days.

(21) Appl. No.: 10/332,776

(22) PCT Filed: Jun. 26, 2001

(86) PCT No.: PCT/GB01/02822

§ 371 (c)(1),
(2), (4) Date: Jan. 13, 2003

(87) PCT Pub. No.: WO02/04389

PCT Pub. Date: Jan. 17, 2002

(65) Prior Publication Data

US 2004/0015031 A1 Jan. 22, 2004

(30) Foreign Application Priority Data

Jul. 12, 2000 (GB) ................................. 0017173.6

(51) Int. Cl.
*C07C 4/06* (2006.01)

(52) U.S. Cl. ...................... 585/324; 585/651; 585/652

(58) Field of Classification Search ................ 585/324, 585/651, 652
See application file for complete search history.

(56) References Cited

U.S. PATENT DOCUMENTS 4,537,873 A * 8/1985 Kato et al. .................. 502/242
5,527,979 A    6/1996 Agaskar et al.

FOREIGN PATENT DOCUMENTS

WO    WO 00 14036 A    3/2000

* cited by examiner

*Primary Examiner*—Thuan D Dang
(74) *Attorney, Agent, or Firm*—Nixon & Vanderhye

(57) ABSTRACT

Process for the production of olefins such as ethylene from a hydrocarbon such as ethane. The process involves passing a mixture of the hydrocarbon and an oxagen-containing gas through a catalyst zone which is capable of supporting combustion beyond the fuel rich limit of flammability to produce the olefin. The catalyst zone comprises at least a first catalyst bed and a second catalyst bed. The second catalyst bed is located downstream of the first catalyst bed, is of a different composition to the first catalyst bed and comprises at least one metal selected from the group consisting of Mo, W, and groups IB, IIB, IIIB, IVB, VB, VIIB and VIII of the Periodic Table. Suitably, the first catalyst bed comprises platinum and the second catalyst bed comprises tin- or copper-promoted nickel, cobalt or iridium catalyst or a copper-only catalyst.

31 Claims, 7 Drawing Sheets

PROCESS FOR THE PRODUCTION OF OLEFINS

BACKGROUND OF THE INVENTION

The present invention relates to a process for the production of olefins.

Olefins such as ethylene and propylene may be produced by the catalytic dehydrogenation or cracking of a hydrocarbon feed. In this specification the term "cracking" will be used to embrace both of these chemical reactions.

The cracking of hydrocarbons is an endothermic process. Accordingly, heat has to be consumed for the reaction to occur. In a process known as auto-thermal cracking, the heat required for cracking is generated by combusting a portion of the original feed stock. This is achieved by passing a mixture of a hydrocarbon feed and an oxygen-containing gas over catalyst capable of supporting combustion beyond the fuel rich limit of flammability. The hydrocarbon feed is partially combusted, and the heat produced by the combustion reaction is used to drive the cracking of the remainder of the feed. An example of an auto-thermal cracking process is described in EP-A-0332289.

Generally, in known auto-thermal cracking processes, a reactant stream of a hydrocarbon and an oxygen-containing gas are passed over a single catalyst bed to produce product olefin. Typically, the catalyst bed comprises at least one platinum group metal, for example, platinum, supported on a catalyst support. Recently, research has been conducted on how to improve the selectivity of these catalysts to olefin product. One method is to modify the catalysts with a metal promoter from Groups IIIA, IVA, VA of the Periodic Table and/or from the transition metals. For example, WO 97/26987 discloses that the selectivity of platinum catalysts may be enhanced by incorporating tin or copper onto the supported platinum catalyst.

In WO 97/26987, the promoted platinum catalysts are prepared by impregnating a catalyst support in a platinum-containing solution, and thereafter into a solution containing the tin or copper promoter. As a result, the platinum and copper or tin promoter are distributed uniformly throughout the support. After prolonged use, however, the concentration of promoter on the support may decrease through evaporation, leading to a loss of activity.

According to Journal of Catalysis 191, 62–74 (2000), the problem of loss of promoter may be addressed by adding the tin to the catalyst by an on-line addition technique. More specifically, an aqueous solution of $SnCl_2$ may be added to the hot operating catalyst support to deposit a thin coating of metal on to the front surface of the support. This compensates for the loss of tin due to evaporation, and restores the catalyst's initial performance. This in-situ regeneration technique is also described in Catalysis Letters 63 (1999), 113–120.

The catalytic behaviour of a supported $Cr_2O_3$ catalyst is studied in detail in Applied Catalysis A (1999), 187(1), 13–24. This reference proposes the theory that the $Cr_2O_3$ catalyst exhibits a distinctive boundary between the oxidising environment at the front of the catalyst and the reducing environment at the rear of the catalyst. In the oxidising environment near the front face of the catalyst, the catalyst acts as an oxidative dehydrogenation catalyst. Once the majority of the oxygen has been consumed at the front end of the catalyst, however, $Cr_2O_3$ acts as a dehydrogenation catalyst, using the heat generated by oxidation reactions at the front of the catalyst to crack the hydrocarbon feed. To support this premise, a Pt-coated monolith was placed in front of a series of $Cr_2O_3$ monoliths. At high $C_2H_6/O_2$ ratios, the arrangement showed higher $C_2H_4$ selectivities than the Pt-monolith alone, confirming that $Cr_2O_3$ can utilise heat generated by the exothermic oxidative reactions occurring over the Pt-monolith to crack any unreacted hydrocarbon in the feed.

The teaching of Applied Catalysis A (1999), 187(1), 13–24, however, is very specific to $Cr_2O_3$. There is nothing in the reference to suggest that other catalyst beds could be employed to increase olefin selectivity in a corresponding manner.

SUMMARY OF THE INVENTION

We have now found that the selectivity of a catalyst zone comprising a catalyst bed (a first catalyst bed) can be enhanced by positioning a second catalyst bed comprising at least one metal selected from the group consisting of Mo, W, and Group IB, IIB, IIIB, IVB, VB, VIIB and VIII of the Periodic Table downstream of the first catalyst bed.

In particular, it has been surprisingly found that the use of a catalyst zone which comprises as the second catalyst bed, a catalyst which is substantially incapable of supporting combustion beyond the fuel rich limit of flammability (that is, a catalyst which is substantially inactive under auto-thermal process conditions), and as the first catalyst bed, a catalyst which is substantially capable of supporting combustion beyond the fuel rich limit of flammability, generally achieves greater olefin selectivity compared to that obtained by the use of the first catalyst bed alone.

Accordingly, the present invention provides a process for the production of an olefin, said process comprising passing a mixture of a hydrocarbon and an oxygen-containing gas through a catalyst zone which is capable of supporting combustion beyond the fuel rich limit of flammability to produce said olefin, said catalyst zone comprising at least a first catalyst bed and a second catalyst bed, and wherein the second catalyst bed is located downstream of the first catalyst bed, is of a different composition to the first catalyst bed and comprises at least one metal selected from the group consisting of Mo, W, and Groups IB, IIB, IIIB, IVB, VB, VIIB and VIII of the Periodic Table.

Preferably, the first catalyst bed comprises a catalyst which is capable of supporting combustion beyond the fuel rich limit of flammability. Suitably, the first catalyst bed may comprise a Group VIII metal. Suitable Group VIII metals include platinum, palladium, ruthenium, rhodium, osmium and iridium. Preferably, the Group VIII metal is selected from rhodium, platinum, palladium or mixtures thereof. Especially preferred are platinum, palladium or mixtures thereof. Typical Group VIII metal loadings range from 0.01 to 100 wt %, preferably, from 0.01 to 20 wt %, and more preferably, from 0.01 to 10 wt %, for example 1–5 wt %, such as 3–5 wt %. Suitably, the first catalyst bed is platinum or palladium, especially platinum.

Alternatively, the first catalyst bed may comprise a promoted catalyst such as a promoted Group VIII metal catalyst. The promoter may be selected from the elements of Groups IIIA, IVA and VA of the Periodic Table and mixtures thereof. Alternatively, the promoter may be a transition metal; the transition metal being a different metal to the metal(s), such as the Group VIII metal(s) employed as the catalytic component.

Preferred Group IIIA metals include Al, Ga, In and Tl. Of these, Ga and In are preferred. Preferred Group IVA metals include Ge, Sn and Pb. Of these, Ge and Sn are preferred, especially Sn. The preferred Group VA metal is Sb. The atomic ratio of Group VIII metal to the Group IIIA, IVA or VA metal may be 1:0.1–50.0, preferably, 1:0.1–12.0, such as 1:0.3–5.

Suitable transition metal promoters may be selected from any one or more of Groups IB to VIII of the Periodic Table. In particular, transition metals selected from Groups IB, IIB, VIB, VIIB and VIII of the Periodic Table are preferred. Examples of such transition metal promoters include Cr, Mo, W, Fe, Ru, Os, Co, Rh, Ir, Ni, Pt, Cu, Ag, Au, Zn, Cd and Hg. Preferred transition metal promoters are Mo, Rh, Ru, Ir, Pt, Cu and Zn, especially Cu. The atomic ratio of the Group VIII metal to the transition metal promoter may be 1:0.1–50.0, preferably, 1:0.1–12.0.

Specific examples of promoted Group III catalysts for use as the first catalyst bed include Pt/Ga, Pt/In, Pt/Sn, Pt/Ge, Pt/Cu, Pd/Sn, Pd/Ge, Pd/Cu and Rh/Sn. Where the Group VIII metal is Rh, Pt or Pd, the Rh, Pt or Pd may comprise between 0.01 and 5.0 wt %, preferably, between 0.01 and 2.0 wt %, and more preferably, between 0.05 and 1.0 wt % of the total weight of the catalyst. The atomic ratio of Rh, Pt or Pd to the Group IIIA, IVA, VA or transition metal promoter may be 1:0.1–50.0, preferably, 1: 0.1–12.0. For example, atomic ratios of Rh, Pt or Pd to Sn may be 1:0.1 to 50, preferably, 1:0.1–12.0, more preferably, 1:0.2–3.0 and most preferably, 1:0.5–1.5. Atomic ratios of Pt or Pd to Ge may be 1:0.1 to 50, preferably, 1:0.1–12.0, and more preferably, 1:0.5–8.0. Atomic ratios of Pt or Pd to Cu may be 1:0.1–3.0, preferably, 1:0.2–2.0, and more preferably, 1:0.5–1.5.

The second catalyst bed comprises at least one metal selected from the group consisting of Mo, W, and Groups IB, IIB, IIIB, IVB, VB, VIIB and VIII of the Periodic Table. In particular, the second catalyst bed may comprise a Group VIII metal as catalyst. Suitable Group VIII metals include platinum, palladium, ruthenium, rhodium, osmium, iridium, cobalt and nickel. Preferably, the Group VIII metal is selected from rhodium, platinum, palladium or mixtures thereof. Particularly preferred are platinum, palladium or mixtures thereof, especially platinum. Typical Group VIII metal loadings range from 0.01 to 100 wt %, preferably, from 0.01 to 20 wt %, and more preferably, from 0.01 to 10 wt %, for example 1–5 wt %, such as 3–5 wt %.

Preferably, the second catalyst bed comprises a promoted catalyst such as a promoted Group VIII metal catalyst. The promoter may be selected from the elements of Groups IIIA, IVA and VA of the Periodic Table and mixtures thereof. Alternatively, the promoter may be a transition metal; said transition metal being a different metal to the Group VIII metal(s) employed as the catalytic component.

Preferred Group IIIA metals include Al, Ga, In and Tl. Of these, Ga and In are preferred. Preferred Group IVA metals include Ge, Sn and Pb. Of these, Ge and Sn are preferred, especially Sn. The preferred Group VA metal is Sb. The atomic ratio of Group VIII metal to the Group IIIA, IVA or VA metal may be 1:0.1–50.0, preferably, 1:0.1–12.0, such as 1:0.3–5.

Suitable transition metal promoters may be selected from any one or more of Groups IB to VIII of the Periodic Table. In particular, transition metals selected from Groups IB, IIB, VIB, VIIB and VIII of the Periodic Table are preferred. Examples of such transition metal promoters include Cr, Mo, W, Fe, Ru, Os, Co, Rh, Ir, Ni, Pt, Cu, Ag, Au, Zn, Cd and Hg. Preferred transition metal promoters are Mo, Rh, Ru, Ir, Pt, Cu and Zn, especially Cu. The atomic ratio of the Group VIII metal to the transition metal promoter may be 1:0.1–50.0, preferably, 1:0.1–12.0.

Specific examples of promoted Group VIII catalysts for use as the second catalyst bed include Pt/Ga, Pt/In, Pt/Sn, Pt/Ge, Pt/Cu, Pd/Sn, Pd/Ge, Pd/Cu and Rh/Sn. Where the Group VIII metal is Rh, Pt or Pd, the Rh, Pt or Pd may comprise between 0.01 and 5.0 wt %, preferably, between 0.01 and 2.0 wt %, and more preferably, between 0.05 and 1.0 wt % of the total weight of the catalyst. The atomic ratio of Rh, Pt or Pd to the Group IIIA, IVA, VA or transition metal promoter may be 1:0.1–50.0, preferably, 1: 0.1–12.0. For example, atomic ratios of Rh, Pt or Pd to Sn may be 1:0.1 to 50, preferably, 1:0.1–12.0, more preferably, 1:0.2–3.0 and most preferably, 1:0.5–1.5. Atomic ratios of Pt or Pd to Ge may be 1:0.1 to 50, preferably, 1:0.1–12.0, and more preferably, 1:0.5–8.0. Atomic ratios of Pt or Pd to Cu may be 1:0.1–3.0, preferably, 1:0.2–2.0, and more preferably, 1:0.5–1.5.

For the avoidance of doubt, the Group VIII metal and promoter in the catalyst beds may be present in any form, for example, as a metal, or in the form of a metal compound, such as an oxide.

The second catalyst bed may comprise a catalyst, such as a Group VIII metal catalyst, which is capable of supporting combustion beyond the fuel-rich limit of flammability. However, whilst such catalysts are useful in certain applications, it may be particularly advantageous to use as the second catalyst bed, a catalyst which is substantially incapable of supporting combustion beyond the fuel rich limit of flammability. Catalysts which are substantially incapable of supporting combustion beyond the fuel rich limit of flammability may be selected from a wide range of known materials including conventional dehydrogenation catalysts. Dehydrogenation catalysts are those catalysts which are capable of converting saturated hydrocarbons to olefins, but are substantially incapable of causing partial combustion of the hydrocarbon feed to olefin under auto-thermal conditions. Thus, suitably, the second catalyst bed may comprise at least one metal selected from Fe, Ru, Os, Co, Ir, Ni, Mo, W, and Groups IB, IIB, IIIB, IVB, VB and VIIB of the Periodic Table. Specific examples of such metals include Cu, Ag, Au, Zn, Cd, Hg, Sc, Y La, Ti, Zr, Hf, V, Nb, Ta, Ni, Co, Ir and mixtures thereof, especially Cu, Co, Ni, Ir and mixtures thereof.

Preferably, catalysts comprising at least one metal selected from Fe, Ru, Os, Co, Ir, Ni, Mo, W, and Groups IB, IIB, IIIB, IVB, VB and VIIB of the Periodic Table are promoted with at least one promoter selected from Group IVA and the transition metals. Suitable Group IVA promoters include Ge, Sn and Pb, preferably Sn. Suitable transition metal promoters include Cr and Cu. Specific examples of suitable catalysts (and which are substantially incapable of causing partial combustion of the hydrocarbon feed to olefin under auto-thermal conditions) for use as the second catalyst bed include Ni/Sn, Co/Sn, Co/Cu, Cu/Cr, Ir/Sn, Fe/Sn, Ru/Sn, Ni/Cu, Cr/Cu, Ir/Cu, Fe/Cu and Ru/Cu.

Suitably, the catalyst zone comprises a first catalyst bed which is capable of supporting combustion beyond the fuel rich limit of flammability and a second catalyst bed which is substantially incapable of supporting combustion beyond the fuel rich limit of flammability.

A particularly advantageous catalyst zone comprises a second catalyst bed selected from Ni/Sn, Co/Sn, Co/Cu, Cu/Cr, Ir/Sn and Cu and a first catalyst bed of a supported platinum-only catalyst.

Alternatively, the catalyst zone may comprise a first and a second catalyst bed, both of which are capable of supporting combustion beyond the fuel rich limit of flammability. Suitably, the first and second catalyst beds may comprise a Group VIII metal such as Rh, Pt or Pd provided that the second catalyst bed is of a different composition to the first catalyst bed. Suitably, the first catalyst may be Rh, Pd or Pt and the second catalyst bed may be, for example, a promoted Group VIII metal for example, Group VIII metals promoted with copper or tin, such as Pt/Sn. Specific examples of such catalyst zones are those comprising a Pt-only catalyst (as first catalyst bed) and a Pt/Sn catalyst (as second catalyst bed).

The catalyst zone may also comprise a first catalyst bed which is substantially incapable of supporting combustion beyond the fuel rich limit of flammability and a second catalyst bed which is substantially capable of supporting combustion beyond the fuel rich limit of flammability. Specific examples of such a catalyst zone include a first catalyst bed selected from Ni/Sn, Co/Sn, Co/Cu, Cu/Cr, Ir/Sn and Cu and a second catalyst bed selected from Pt or Pd or promoted Pt or Pd such as Pt or Pd promoted with copper or tin.

In addition to the first and second catalyst beds the catalyst zone may comprise further catalyst beds. For example, the catalyst zone may comprise 3 to 10, preferably, 3 to 5 catalyst beds.

Where the catalyst zone comprises more than two catalyst beds, the catalyst of the additional bed(s) may be the same or different to the catalysts used for either of the first and second catalyst beds. Suitably, the catalyst used for the additional bed(s) is the same as that of the second catalyst bed. For example, the catalyst zone may comprise 3 catalyst beds wherein the first bed is platinum and the second and third beds both comprise tin-promoted nickel.

It should be understood that actual concentrations of metal in the catalysts tend not to be identical to the nominal concentrations employed in the preparation of the catalyst because not all the metal employed during the preparation of the catalyst actually becomes incorporated in the catalyst composition. Thus, the nominal metal concentrations may have to be varied to ensure that the desired actual metal concentrations are achieved. Generally, however, the catalyst beds are prepared such that the actual concentration of a particular metal is between 80 and 99%, preferably, between 90 and 99% of the nominal value.

Each catalyst employed in the catalyst zone may be unsupported or supported. Suitably, an unsupported catalyst may be in the form of a metal gauze. Preferably, at least one catalyst in the catalyst zone is a supported catalyst. Suitably, each catalyst in the catalyst zone is a supported catalyst. The support used for each catalyst may be the same or different. Although a range of support materials may be used, ceramic supports are generally preferred. However, metal supports may also be used.

Suitably, the ceramic support may be any oxide or combination of oxides that is stable at high temperatures of, for example, between 600° C. and 1200° C. The ceramic support material preferably has a low thermal expansion co-efficient, and is resistant to phase separation at high temperatures.

Suitable ceramic supports include cordierite, lithium aluminium silicate (LAS), alumina (alpha-$Al_2O_3$), yttria stabilised zirconia, aluminium titanate, niascon, and calcium zirconyl phosphate, and, in particular, alumina.

The ceramic support may be wash-coated, for example, with gamma-$Al_2O_3$.

The structure of the support material is important, as the structure may affect flow patterns through the catalyst. Such flow patterns may influence the transport of reactants and products to and from the catalyst surface, thereby affecting the activity of the catalyst. Typically, the support material may be in the form of particles, such as spheres or other granular shapes or it may be in the form of a foam or fibre such as a fibrous pad or mat. Suitably, the particulate support material may be alumina spheres. Preferably, the form of the support is a monolith which is a continuous multi-channel ceramic structure. Such monoliths include honeycomb structures, foams, or fibrous pads. The pores of foam monolith structures tend to provide tortuous paths for reactants and products. Such foam monolith supports may have 20 to 80, preferably, 30 to 50 pores per inch. Channel monoliths generally have straighter, channel-like pores. These pores are generally smaller, and there may be 80 or more pores per linear inch of catalyst.

Preferred ceramic foams include alumina foams.

Alternatively, the support may be present as a thin layer or wash coat on another substrate.

Where a supported catalyst is employed, the metal components of the catalyst are preferably distributed substantially uniformly throughout the support The catalysts employed in the present invention may be prepared by any method known in the art. For example, gel methods and wet-impregnation techniques may be employed. Typically, the support is impregnated with one or more solutions comprising the metals, dried and then calcined in air. The support may be impregnated in one or more steps. Preferably, multiple impregnation steps are employed. The support is preferably dried and calcined between each impregnation, and then subjected to a final calcination, preferably, in air. The calcined support nay then be reduced, for example, by heat treatment in a hydrogen atmosphere.

The catalyst zone may be achieved in any suitable manner provided that the reactant stream (hydrocarbon and oxygen-containing gas) contacts the first catalyst bed bed thereby producing an effluent stream (comprising reaction products and unreacted feed) therefrom, and said effluent stream passes from the first catalyst bed to the second catalyst bed. A convenient method of achieving the catalyst zone is to use a single reactor with a space being provided between the beds. The space can be provided by placing substantially inert materials such as alumina, silica, or other refractory materials between the catalyst beds.

Alternatively, the space between the catalyst beds is a substantial void.

The space between the catalyst beds is not critical in relation to the beds. Preferably, however, the space will be as small as practical. Most preferably, there is no substantial space between the catalyst beds, that is, the beds are directly adjacent to one another. Where the catalyst zone comprises more than two beds, the size of the space between the beds may vary.

The size of the catalyst beds can vary one from the other.

The catalyst beds may be arranged either vertically or horizontally.

The hydrocarbon may be any hydrocarbon which can be converted to an olefin, preferably a mono-olefin, under the partial combustion conditions employed.

The process of the present invention may be used to convert both liquid and gaseous hydrocarbons into olefins. Suitable liquid hydrocarbons include naphtha, gas oils, vacuum gas oils and mixtures thereof. Preferably, however, gaseous hydrocarbons such as ethane, propane, butane and mixtures thereof are employed. Suitably, the hydrocarbon is a paraffin-containing feed comprising hydrocarbons having at least two carbon atoms.

The hydrocarbon feed is mixed with any suitable oxygen-containing gas. Suitably, the oxygen-containing gas is molecular oxygen, air, and/or mixtures thereof. The oxygen-containing gas may be mixed with an inert gas such as nitrogen or argon.

Additional feed components may be included, if so desired. Suitably, methane, hydrogen, carbon monoxide, carbon dioxide or steam may be co-fed into the reactant stream.

Any molar ratio of hydrocarbon to oxygen-containing gas is suitable provided the desired olefin is produced in the process of the present invention. The preferred stoichiometric ratio of hydrocarbon to oxygen-containing gas is 5 to 16, preferably, 5 to 13.5 times, preferably, 6 to 10 times the stoichiometric ratio of hydrocarbon to oxygen-containing gas required for complete combustion of the hydrocarbon to carbon dioxide and water.

The hydrocarbon is passed over the catalyst at a gas hourly space velocity of greater than 10,000 $h^{-1}$, preferably above 20,000 $h^{-1}$ and most preferably, greater than 100,000 $h^{-1}$. It will be understood, however, that the optimum gas hourly space velocity will depend upon the pressure and nature of the feed composition.

Preferably, hydrogen is co-fed with the hydrocarbon and oxygen-containing gas into the reaction zone. The molar ratio of hydrogen to oxygen-containing gas can vary over any operable range provided that the desired olefin product is produced. Suitably, the molar ratio of hydrogen to oxygen-containing gas is in the range 0.2 to 4, preferably, in the range -1 to 3.

Hydrogen co-feeds are advantageous because, in the presence of the catalyst, the hydrogen combusts preferentially relative to the hydrocarbon, thereby increasing the olefin selectivity of the overall process.

Preferably, the reactant mixture of hydrocarbon and oxygen-containing gas (and optionally hydrogen co-feed) is preheated prior to contact with the catalyst. Generally, the reactant mixture is preheated to temperatures below the autoignition temperature of the reactant mixture.

Advantageously, a heat exchanger may be employed to preheat the reactant mixture prior to contact with the catalyst. The use of a heat exchanger may allow the reactant mixture to be heated to high preheat temperatures such as temperatures at or above the autoignition temperature of the reactant mixture. The use of high pre-heat temperatures is beneficial in that less oxygen reactant is required which leads to economic savings. Additionally, the use of high preheat temperatures can result in improved selectivity to olefin product. It has also be found that the use of high preheat temperatures enhances the stability of the reaction within the catalyst thereby leading to higher sustainable superficial feed velocities.

It should be understood that the autoignition temperature of a reactant mixture is dependent on pressure as well as the feed composition: it is not an absolute value. Typically, in auto-thermal cracking processes, where the hydrocarbon is ethane at a pressure of 2 atmospheres, a preheat temperature of up to 450° C. may be used.

The process of the present invention may suitably be carried out at a catalyst exit temperature in the range 600° C. to 1200° C., preferably, in the range 850° C. to 1050° C. and, most preferably, in the range 900° C. to 1000° C.

The process of the present invention may be carried out at atmospheric or elevated pressure. Suitably, the pressure may be in the range from 0 to 2 bara, preferably 1.5 to 2 bara, for example 1.8 bara. Elevated pressures of, for example, 2 to 50 bara, may also be suitable.

Where the process of the present invention is carried out at elevated pressure, the reaction products may be quenched as they emerge from the reaction chamber to avoid further reactions taking place.

Any coke produced in the process of the present invention may be removed by mechanical means, or by using one of the decoking methods such as that described in EP-A-0 709 446, the contents of which are hereby incorporated by reference.

BRIEF DESCRIPTION OF THE DRAWINGS

The invention will now be illustrated by way of example only and with reference to FIG. 1 and to the following examples.

DETAILED DESCRIPTION OF PREFERRED EMBODIMENTS

Figure 1:
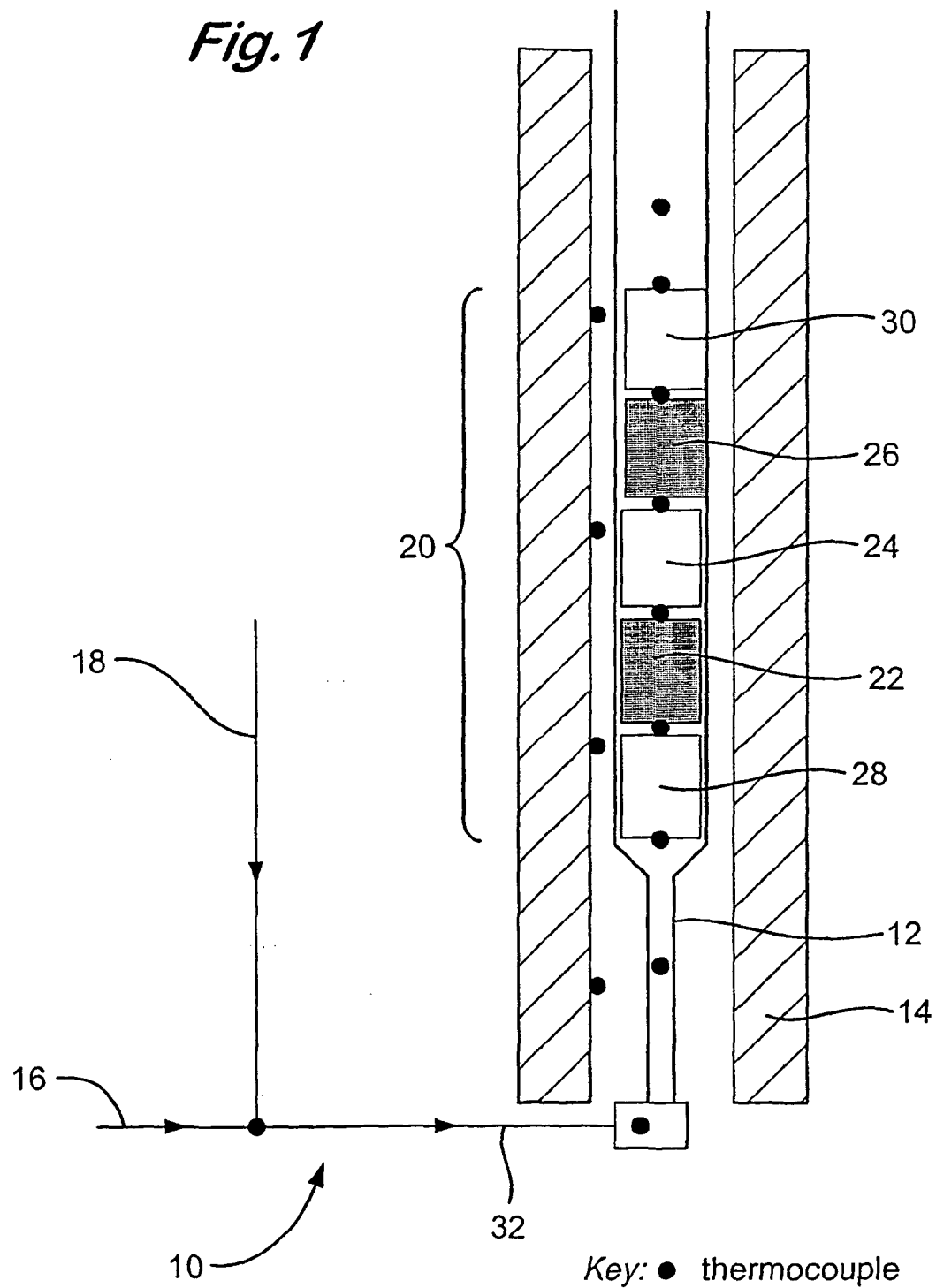
FIG. 1 represents in schematic form, an apparatus suitable for use in the process of the present invention.

FIG. 1 depicts an apparatus 10 comprising a quartz reactor 12 surrounded by an electrically-heated furnace 14. The reactor 12 is coupled to an oxygen-containing gas supply 16 and a hydrocarbon feed supply 18. Optionally, the hydrocarbon feed may comprise a co-feed such as hydrogen and a diluent such as nitrogen. In use, the reactor 12 is provided with a catalyst zone 20 which is capable of supporting combustion beyond the fuel rich limit of flammability and comprises between one to three catalyst beds, 22, 24 and 26. The catalyst beds 22, 24 and 26 are positioned between LAS heat shields 28, 30.

In use, the furnace 14 is set so as to minimise heat losses, and the reactants are introduced into the reactor via line 32. As the reactants contact the catalyst beds 22, 24, 26, some of the hydrocarbon feed combusts to produce water and carbon oxides. The optional hydrogen co-feed also combusts to produce water. Both of these combustion reactions are exothermic, and the heat produced therefrom is used to drive the cracking of the hydrocarbon to produce olefin.

Catalyst Preparation

Catalyst A (1 wt % Pt on Alumina)

Alumina foam blocks (28 mm diameter by 30 mm deep, 30 pores per inch) were repeatedly impregnated with an aqueous solution of tetrammineplatinum(II) chloride. The tetrammineplatinum(II) chloride solution was prepared with sufficient salt to achieve a nominal Pt loading of 1 wt % if all the metal in the salt were incorporated into the final catalyst formulation. The volume of de-ionised water employed in the tetrammineplatinum solution was equivalent to three times the volume of the alumina foam blocks. Between impregnations excess solution was removed from the foam blocks. The foam blocks were then dried in air at 120–140° C. for approximately 30 minutes, and subsequently calcined in air at 450° C. for approximately 30 minutes (to decompose the Pt salt to Pt metal on the foam surface). Once all the solution had been absorbed onto the foams (typically three impregnations are required) the blocks were dried and given a final air calcination at 1200° C. for 6 hours.

Catalyst B (1 wt % Pt 4 wt % Sn on Alumina)

Alumina foam blocks (99.5% alumina; 28 mm diameter by 30 mm deep, 30 pores per inch) were alternately impregnated with aqueous solutions of tetrammineplatinum(II) chloride and tin(II)chloride/HCl. The aqueous solutions were prepared with sufficient salt to give a final loading of 1 wt % platinum and 4 wt % tin, assuming 100% absorption and with a volume of de-ionised water equivalent to three times the volume of the support materials to be impregnated. Between impregnations excess solution was removed from the foam blocks and the blocks were dried in air at 120–140° C., and then calcined in air at 450° C. for approximately 30 minutes. Once all the solutions had been absorbed onto the foam blocks, the blocks were dried and calcined in air at 600° C. for 6 hours.

Catalyst C (3 wt % Pt on Alumina)

The preparation as for catalyst A was repeated except that the tetra-amineplatinum(II) chloride solution employed was of sufficient concentration to produce a catalyst having a nominal Pt loading of 3 wt %.

Catalyst D (0.2 wt % Ni, 4 wt % Sn on Alumina)

The preparation as for catalyst B was repeated except that the alumina foam blocks were alternately impregnated with aqueous solutions of nickel (II) nitrate and tin (II) chloride/dil HCl of sufficient concentration to produce a catalyst having a nominal loading of 0.2 wt % Ni and 4 wt % tin.

Catalyst E (1 wt % Ni. 4 wt % Sn on Alumina)

The preparation of catalyst D was repeated except that the concentration of the nickel (II) nitrate solution used was such so as to produce a catalyst having a nominal Ni loading of 1 wt %.

Catalyst F (1 wt % Co. 4 wt % Sn on Alumina)

The preparation as for catalyst B was repeated except that the alumina foam blocks were alternately impregnated with aqueous solutions of cobalt (II) nitrate and tin (II) chloride/dil HCl of sufficient concentration to produce a catalyst having a nominal loading of 1 wt % Co and 4 wt % tin.

Catalyst G (1 wt % Co, 0.3 wt % Cu on Alumina)

The preparation as for catalyst B was repeated except that the alumina foam blocks were alternately impregnated with aqueous solutions of cobalt (II) nitrate and copper (II) chloride of sufficient concentration to produce a catalyst having a nominal loading of 1 wt % Co and 0.3 wt % Cu.

Catalyst H (I wt % Pt. 4 wt % Sn on Alumina)

An ethanolic solution was prepared comprising hexachloroplatinic acid $H_2PtCl_6$, tin (II) chloride $SnCl_2$ and a small quantity of hydrochloric acid. The solution contained sufficient platinum and tin salts so as to achieve a final loading of 1 wt % platinum and 4 wt % tin if all salt were absorbed onto the support material during impregnations. The volume of ethanol employed was equivalent to three times the volume of the alumina foam blocks which were to be used as the support material. The alumina foam blocks (30 pores per inch, 28 mm diameter, 30 mm deep) were repeatedly impregnated with the ethanolic solution until all the solution was absorbed onto the blocks (four impregnations were required). Between impregnations excess solution was removed from the foam blocks and the blocks were dried in air at 120–140° C. then calcined in air at 450° C. for approximately 30 minutes. Once all the solutions had been absorbed onto the foam blocks, the blocks were dried and given a final air calcination at 600° C. for 6 hours.

Catalyst I (1 wt % Ir, 0.3 wt % Sn on Alumina)

The preparation as for catalyst B was repeated except that the alumina foam blocks were alternately impregnated with aqueous solutions of iridium (III) chloride and tin (II) chloride/dil HCl of sufficient concentration to produce a catalyst having a nominal loading of 1 wt % Ir and 0.3 wt % Sn.

Catalyst J (3 wt % Pt on Alumina)

The preparation as for catalyst A was repeated except that alumina foam blocks of dimensions 15 mm diameter by 30 mm deep and 30 pores per inch were used and the blocks were impregnated with sufficient concentration of tetrammineplatinum(II) chloride solution to achieve a nominal Pt loading of 3 wt %.

Catalyst K (1 wt % Cu on Alumina)

The preparation as for catalyst A was repeated except that alumina foam blocks of dimensions 15 mm diameter by 30 mm deep and 30 pores per inch were used and the blocks were impregnated with sufficient concentration of copper(II) nitrate solution to achieve a nominal Cu loading of 1 wt %.

Catalyst L (3 wt % Pt on Alumina Spheres)

Alumina spheres (1.8 mm diameter, surface area approximately 210 $m^2/g$ supplied by Condea) were pre-calcined in air to 1200° C. for 6 hours in order to remove any residual porosity associated with the spheres.

The weight of the spheres to be used in the preparation was measured and the weight of platinum metal required to give the final 'target' platinum loading of 3 wt % was calculated using the equation below:

$$\text{Elemental platinum required }(g) = 3/100 \times \text{Weight of alumina spheres}(g)$$

A quantity of tetrammineplatinum(II) chloride corresponding to the calculated mass of platinum metal was dissolved in a volume of de-ionised water equivalent to the bed volume of the alumina spheres.

The spheres were placed in the platinum solution for approximately 20 minutes. Excess platinum solution was removed and the spheres were transferred to a silica drying tray and moisture was removed in a drying oven set to 120° C. and held at that temperature for 30 minutes. The spheres were then transferred into a calcination oven set to 450° C. and held at 450° C. for 30 minutes, transferred to the drying oven to cool to 120° C. and then allowed to cool back to room temperature. The remaining platinum-solution was then absorbed onto the spheres and the drying and calcination procedure was repeated until all the platinum solution was absorbed onto the spheres.

After the final calcination at 450° C. the spheres were given an additional high temperature calcination at 1200° C. for 6 hours (ramping from 450° C. to 1200° C. at 5° C./min) and then allowed to cool to room temperature.

Catalyst M (1 wt % Cu on Alumina Spheres)

The preparation as for catalyst L was repeated except that the Pt solution was replaced by sufficient copper (II) nitrate solution to give a final target copper loading of 1 wt %.

Experiment 1 (Double Bed—1 wt % Pt on Alumina; 1 wt % Pt on Alumina)

Two catalyst beds of catalyst A were positioned sequentially with respect to one another in the reactor of FIG. 1, as catalyst beds 22 and 24 (catalyst bed 22 being the first catalyst bed). Catalyst bed dimensions were 15 mm diameter, 30 mm depth and porosity 30 pores per inch. Internal diameter of the reactor was 28 mm.

The reactor furnace was set to 750° C.

Figure 2:
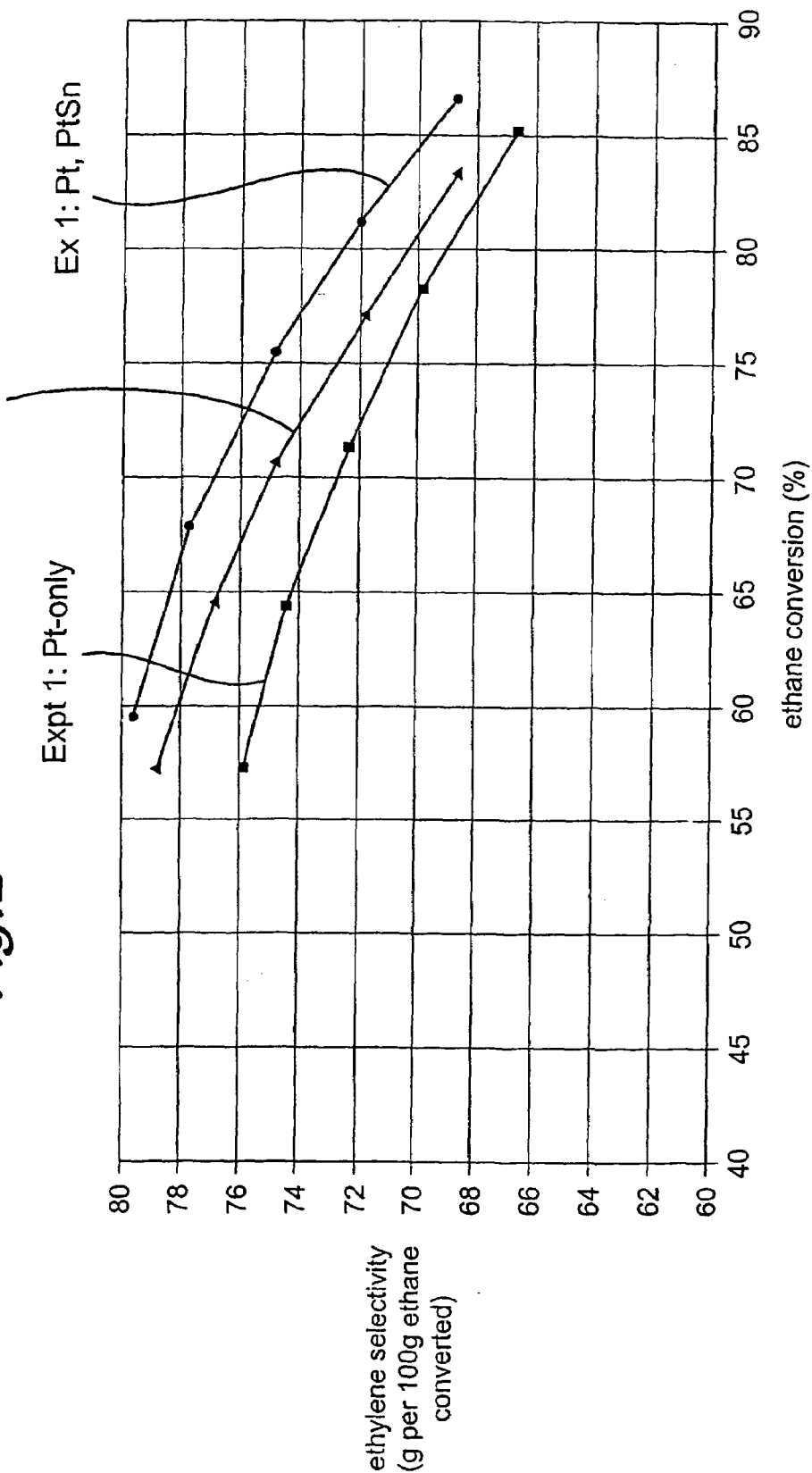
FIG. 2 is a graph showing the effect on ethylene selectivity of using multiple beds of Sn promoted Pt catalyst compared to a single bed of Pt-only catalyst.

Oxygen, ethane, hydrogen and nitrogen were then passed over the catalyst beds at a fixed total gas flow rate of 36.9 nl/min. The gas flow rates were controlled using thermal mass flow controllers supplied by Bronkhorst HiTech BV. The volumetric H2:O2 feed ratio was maintained at a ratio of approximately 2:1, whilst the concentration of nitrogen in the feed was maintained at 10% to allow mass balance work-up. During the course of the reaction, the oxygen:ethane feed ratio was adjusted, so as to vary the ethane conversion rate from approximately 40 to 90%. Corresponding changes in ethylene selectivity were measured and the results are shown in FIG. 2 below.

The product composition was analysed by gas chromatography equipped with thermal conductivity and flame ionisation detectors.

EXAMPLES

Example 1 (Double Bed—1 wt % Pt on Alumina; 1 wt % Pt. 4 wt % Sn on Alumina)

Experiment 1 was repeated except that catalyst A was used as catalyst bed 22, and catalyst B was used as catalyst bed 24 and prior to reaction the catalyst beds 22 and 24 were reduced in situ by passing approximately 1.0 nl/min of hydrogen and 1.5 nl/min of nitrogen over the beds at 750° C. for 1 hour.

The ethylene selectivities obtained are illustrated in FIG. 2.

It can be seen that a catalyst zone comprising a bed of tin-promoted platinum catalst located downstream of a bed of platinum catalyst gives a higher selectivity to ethylene than that obtained in Experiment 1 where the catalyst zone comprised 2 beds of platinum-only catalyst.

Example 2 (Triple Bed—1 wt % Pt on Alumina; Alumina; 1 wt % Pt, 4 wt % Sn on Alumina)

Example 1 was repeated except that an alumina block was positioned between the catalyst beds 22 and 24. The ethylene selectivities obtained are illustrated in FIG. 2. As can be seen from FIG. 2, the ethylene selectivity obtained using a catalyst zone comprising sequential beds of platinum; alumina and tin-promoted platinum is higher than that obtained from a catalyst zone comprising a single bed of platinum, but lower than that obtained from a catalyst zone comprising a tin-promoted platinum catalyst bed positioned downstream of a platinum-only catalyst bed.

Experiment 2 (Triple Bed—3 wt % Pt; 3 wt % Pt; 3 wt % Pt)

Three beds of catalyst C were loaded sequentially into the reactor of FIG. 1, as catalyst beds 22, 24 and 26. The 3 catalyst beds were then reduced in situ by passing approximately 1.0 nl/min of hydrogen and 1.5 nl/min of nitrogen over the beds at 750° C. for 1 hour.

Oxygen, ethane, hydrogen and nitrogen were then passed over the catalyst beds as described for Experiment 1. The corresponding changes in ethylene selectivity were measured and the results are shown in FIG. 3.

Example 3 (Triple Bed—3 wt % Pt on Alumina; 0.2 wt % Ni, 4 wt % Sn on Alumina; 0.2 wt % Ni, 4 wt % Sn on Alumina Experiment 2 was repeated except that catalyst C was used as catalyst bed 22, and catalyst D was used as catalyst beds 24 and 26 and the 3 beds were reduced in situ by passing approximately 1.0 nl/min of hydrogen and 1.5 nl/min of nitrogen over the beds at 750° C. for 1 hour.

Figure 3:
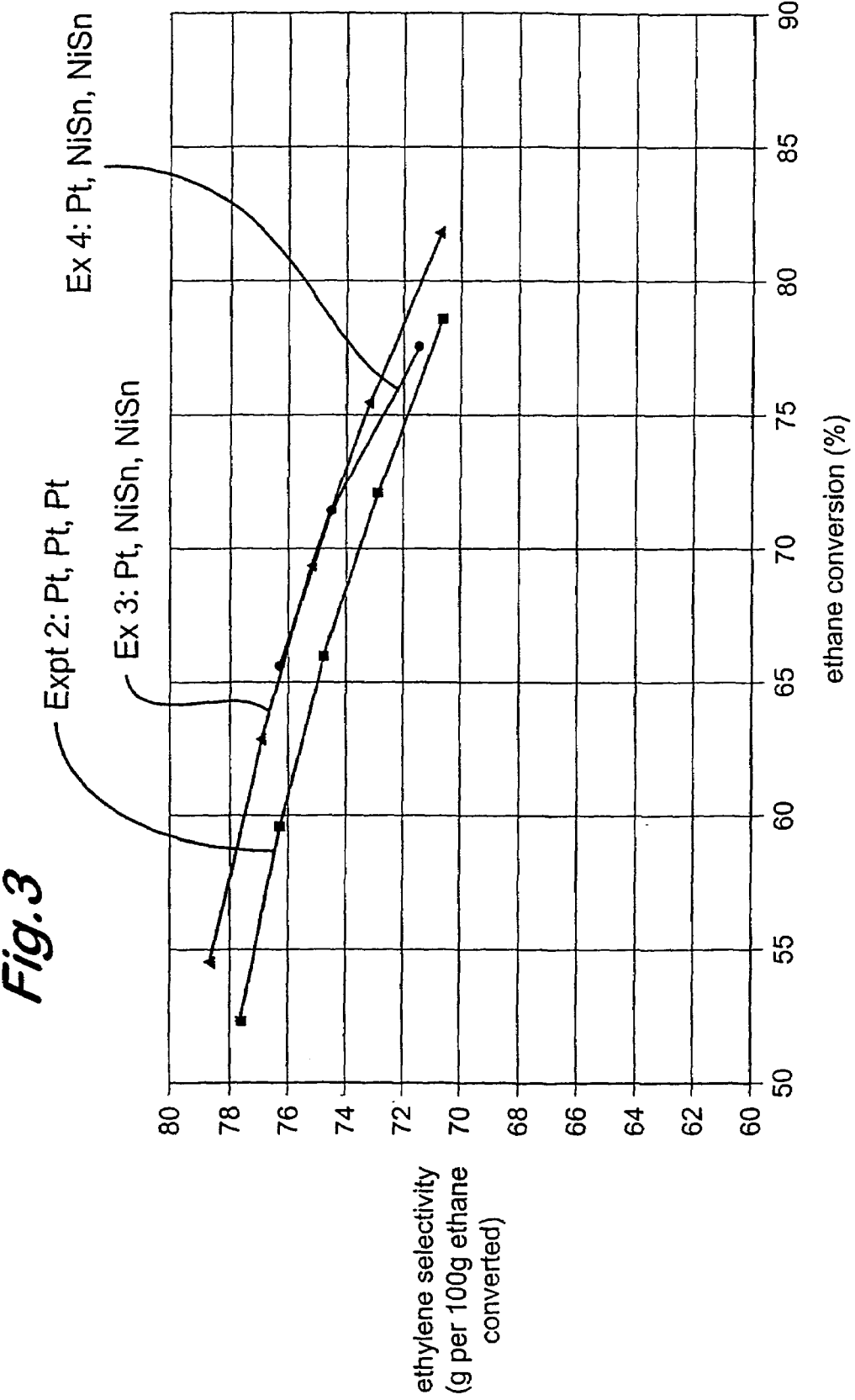
FIG. 3 is a graph showing the effect on ethylene selectivity of using triple beds of Pt and Ni—Sn catalysts compared to a triple bed of Pt-only catalyst.

The ethylene selectivities obtained in Example 3 are illustrated in FIG. 3. The results show that the use of a catalyst zone comprising 2 beds of tin-promoted nickel catalyst placed downstream of a platinum-only catalyst bed leads to higher ethylene selectivity than that observed in Experiment 2 where the catalyst zone comprised 3 Pt-only beds.

Example 4 (Triple Bed—3 wt % Pt on Alumina; 1 wt % Ni, 4 wt % Sn on Alumina; 1 wt % Ni, 4 wt % Sn on Alumina)

Example 3 was repeated except that catalyst E was used as catalyst beds 24 and 26.

The ethylene selectivities obtained in Example 3 are illustrated in FIG. 3. The results show that use of a catalyst zone comprising two 1 wt % Ni, 4 wt % Sn beds downstream of a platinum-only catalyst leads to higher ethylene selectivities than those observed in Experiment 2 where a catalyst zone of 3 Pt-only beds was used. However, compared to the selectivities obtained in Example 3 it can be seen that at higher nickel loadings, selectivities decline to a greater extent at high ethane conversion.

Experiment 3 (Double Bed—3 wt % Pt on Alumina; 3 wt % Pt on Alumina)

Two beds of catalyst C were loaded sequentially into the reactor of FIG. 1, as catalyst beds 22 and 24.

Oxygen, ethane, hydrogen and nitrogen were then passed over the catalyst beds as described for Experiment 1. The corresponding changes in ethylene selectivity were measured and the results are shown in FIG. 4 below.

Example 5 (Double Bed—3 wt % Pt on Alumina; 1 wt % Co, 4 wt % Sn on Alumina)

Experiment 3 was repeated except that catalyst F was used as catalyst bed 24 and catalyst beds 22 and 24 were reduced in situ by passing approximately 1.0 nl/min of hydrogen and 1.5 nl/min of nitrogen over the beds at 750° C. for 1 hour.

Figure 4:
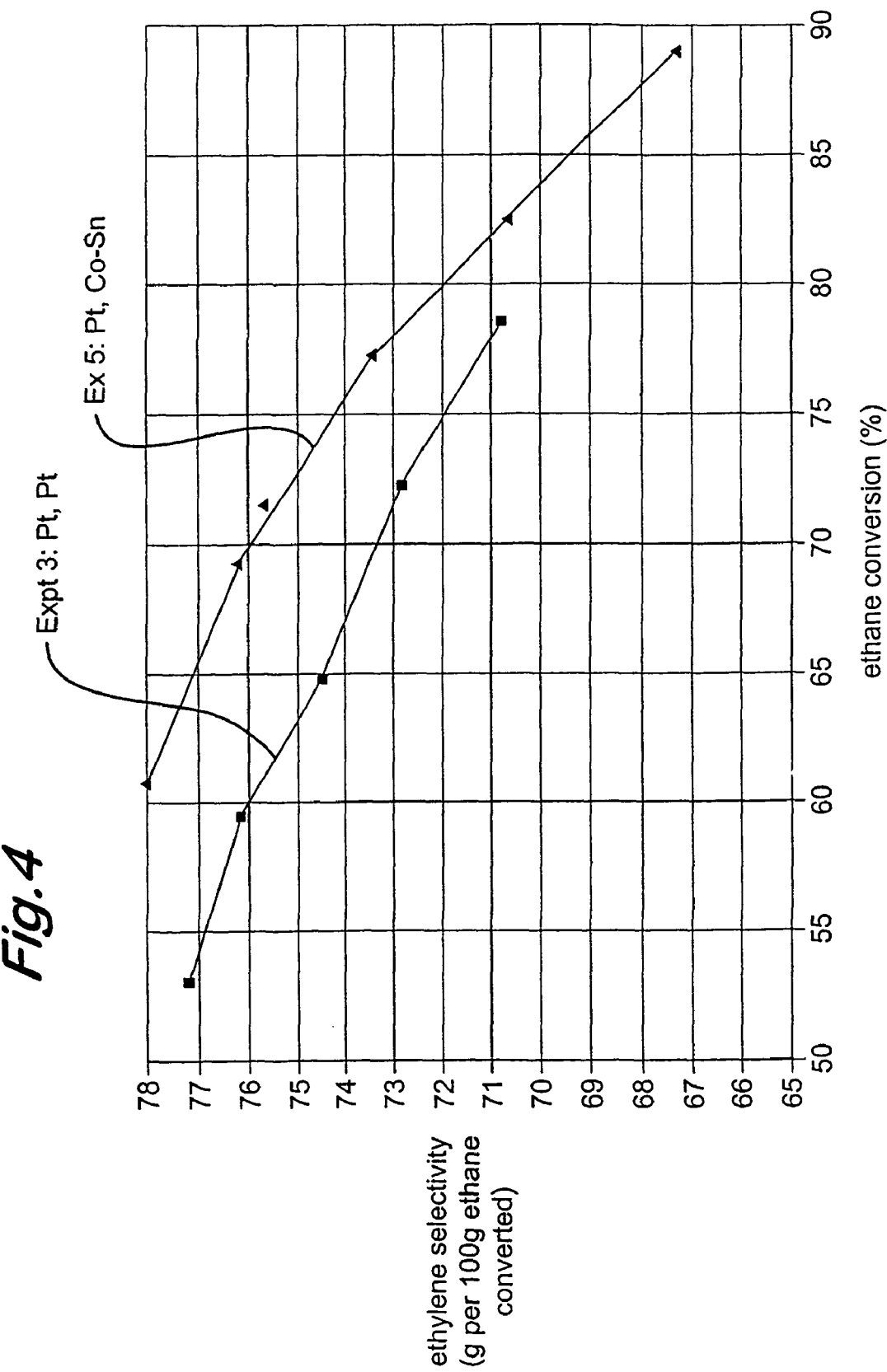
FIG. 4 is a graph showing the effect on ethylene selectivity of using a double bed of Pt and Sn promoted Co catalysts compared to a double bed of Pt-only catalyst.

The ethylene selectivities obtained in Example 5 are illustrated in FIG. 4. The results show that use of a catalyst zone comprising a bed of tin-promoted cobalt catalyst placed downstream of a bed of platinum-only catalyst leads to higher ethylene selectivity relative to that observed in Experiment 3 where a catalyst zone of 2 platinum-only catalyst beds was used.

Experiment 4 (Single Bed—1 wt % Co, 0.3 wt % Cu on Alumina)

Catalyst G was loaded into the reactor of FIG. 1, as the only catalyst bed (22). The catalyst bed was then reduced in situ by passing approximately 1.0 nl/min of hydrogen and 1.5 nl/min of nitrogen over the bed at 750° C. for 1 hour.

Figure 5:
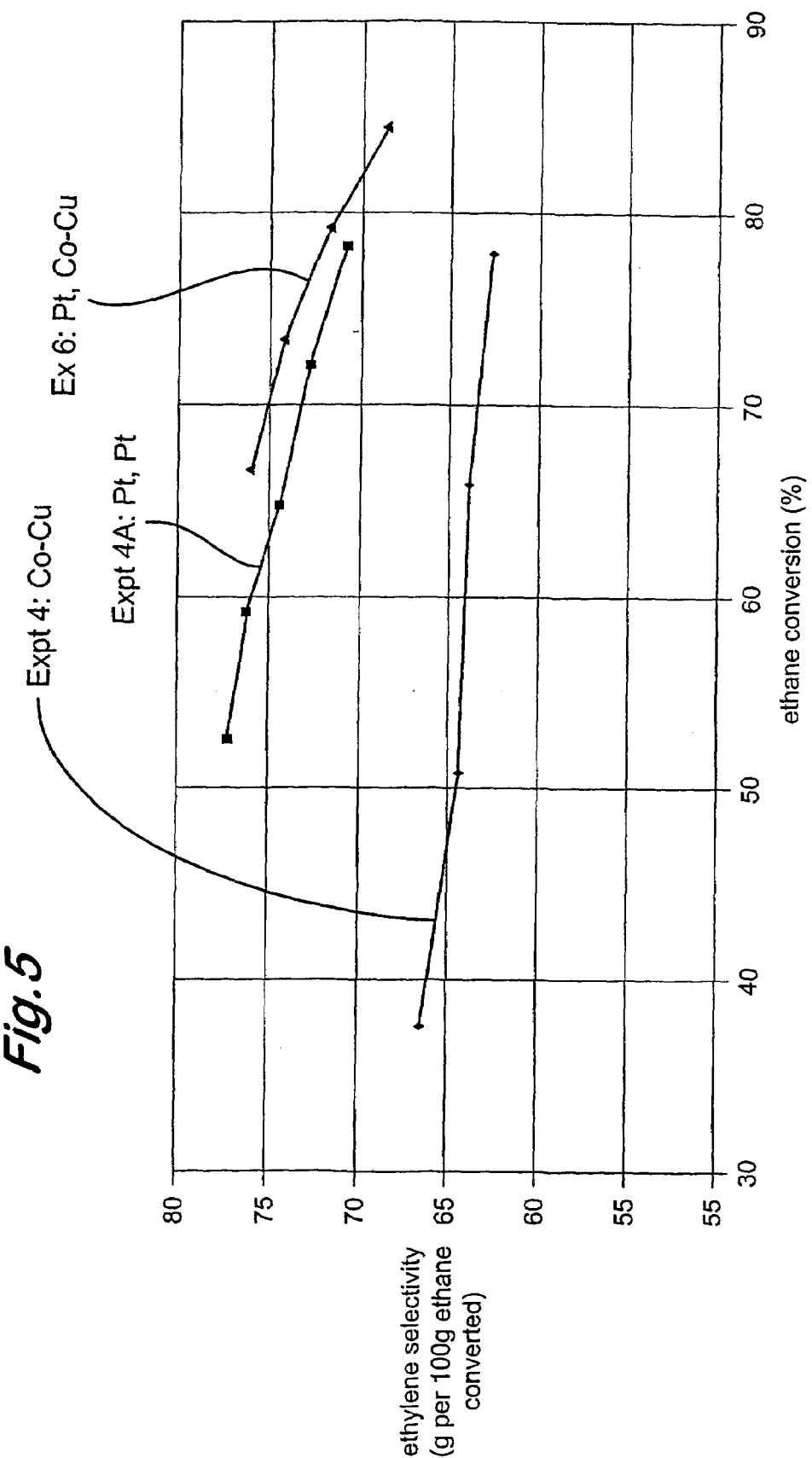
FIG. 5 is a graph showing the effect on ethylene selectivity of using a double bed of Pt and Cu promoted Co catalysts compared to a double bed of Pt-only catalyst and a single bed of Cu promoted Co catalyst

Oxygen, ethane, hydrogen and nitrogen were then passed over the catalyst as described for Experiment 1. The corresponding changes in ethylene selectivity were measured and the results are shown in FIG. 5.

Experiment 4A (Double Bed—3 wt % Pt on Alumina; 3 wt % Pt on Alumina)

Experiment 4 was repeated except that 2 beds of catalyst C (22, 24) were used.

Example 6 (Double Bed—3 wt % Pt on Alumina; 1 wt % Co, 0.3 wt % Cu on Alumina)

Experiment 4 was repeated except that catalyst C was used as catalyst bed 22 and catalyst G was used as catalyst bed 24.

The ethylene selectivities obtained in Example 6 are illustrated in FIG. 5. As can be seen from FIG. 5, the use of a catalyst zone comprising a bed of platinum catalyst and a bed of copper promoted-cobalt catalyst gives superior ethylene selectivity than a catalyst zone comprising a single bed of copper-promoted cobalt catalyst.

Also illustrated in FIG. 5 is the ethylene selectivity obtained in Experiment 4A. It can be seen from FIG. 5 that the ethylene selectivity obtained from a catalyst zone comprising a bed of platinum catalyst and a bed of copper-promoted cobalt catalyst is also superior to that obtained from a catalyst zone comprising 2 beds of platinum-only catalyst.

Experiment 5 (Single Bed—1 wt % Pt, 4 wt % Sn on Alumina)

Catalyst H was loaded into the reactor of FIG. 1, as the only catalyst bed (22). The catalyst bed was then reduced in situ by passing approximately 1.0 nl/min of hydrogen and 1.5 nl/min of nitrogen over the bed at 750° C. for 1 hour.

Figure 6:
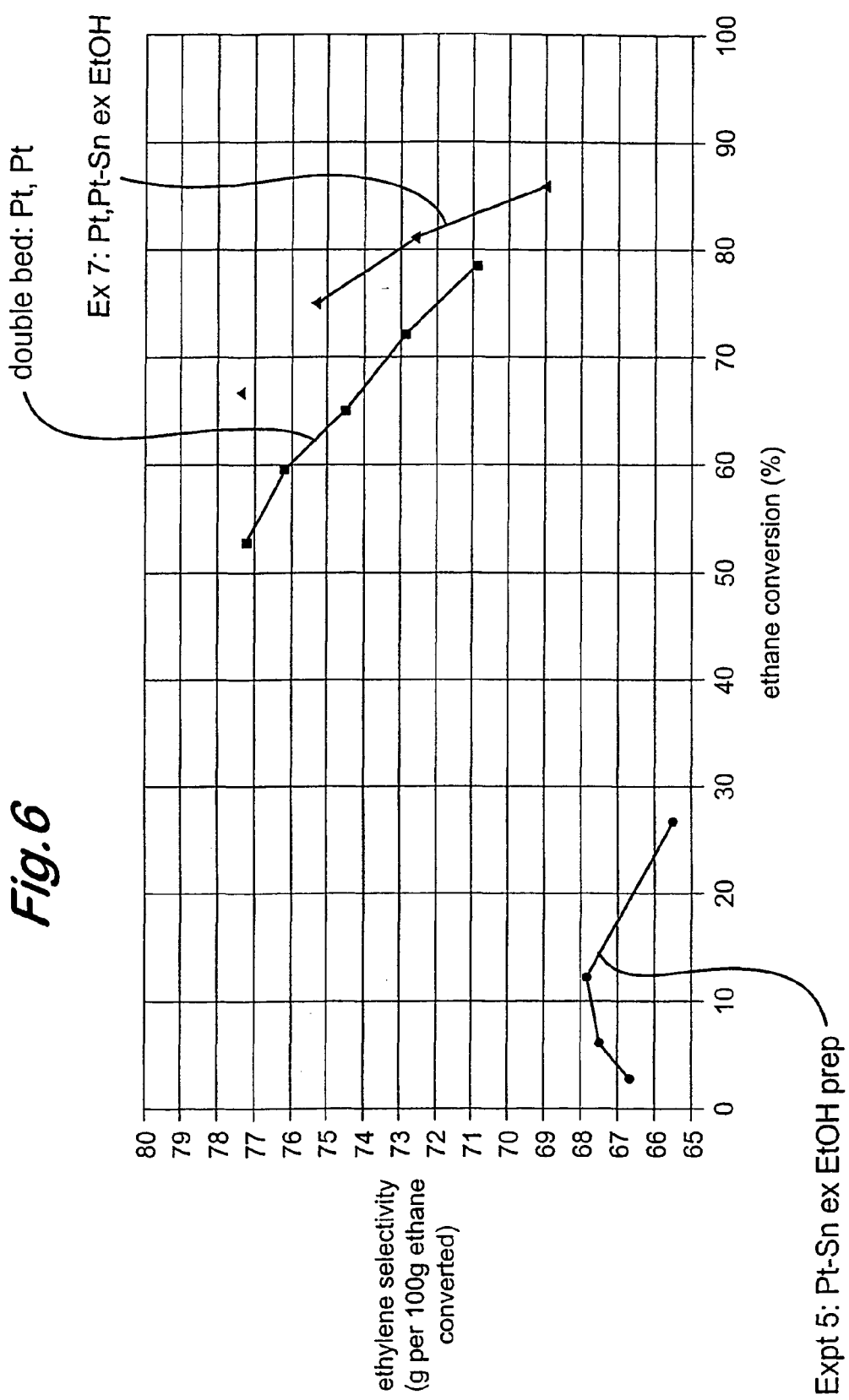
FIG. 6 is a graph showing the effect on ethylene selectivity of using a double bed of Pt, and Sn promoted Pt catalysts compared to single beds of Pt-only and Sn promoted Pt catalysts.

Oxygen, ethane, hydrogen and nitrogen were then passed over the catalyst bed as described for Experiment 1. The corresponding changes in ethylene selectivity were measured and the results are shown in FIG. 6. It can be seen that the olefin selectivities obtained using a catalyst bed prepared using the ethanolic preparation method of catalyst H are relatively poor.

Example 7 (Double Bed—3 wt % Pt on Alumina; 1 wt % Pt, 4 wt % Sn on Alumina)

Experiment 5 was repeated except that two catalyst beds (22, 24) were used. Catalyst C was employed as catalyst bed 22 and catalyst H was used as catalyst bed 24.

The ethylene selectivities obtained in Example 7 are shown in FIG. 6. From inspection of FIG. 6 it can be seen that the use of a catalyst zone comprising a bed of tin-promoted platinum catalyst placed downstream of a platinum-only catalyst bed shows superior olefin selectivity compared to a catalyst zone comprising a single bed of tin-promoted platinum catalyst.

Also illustrated in FIG. 6 are the ethylene selectivities obtained using a catalyst zone comprising two 3 wt % Pt catalyst beds (catalyst C). As can be seen from FIG. 6 the olefin selectivities obtained using a catalyst zone comprising a tin-promoted platinum catalyst bed placed downstream of a platinum-only catalyst bed are superior to those obtained using a catalyst zone comprising two beds of platinum-only catalyst.

Example 8 (Double Bed—3 wt % Pt on Alumina; 1 wt % Ir, 4 wt % Sn on Alumina)

Catalyst C and catalyst I were loaded sequentially into the reactor of FIG. 1 as catalyst beds 22 and 24 respectively. The beds were then reduced in situ by passing approximately 1.0 nl/min of hydrogen and 1.5 nl/min of nitrogen over the beds at 750° C. for 1 hour.

Figure 7:
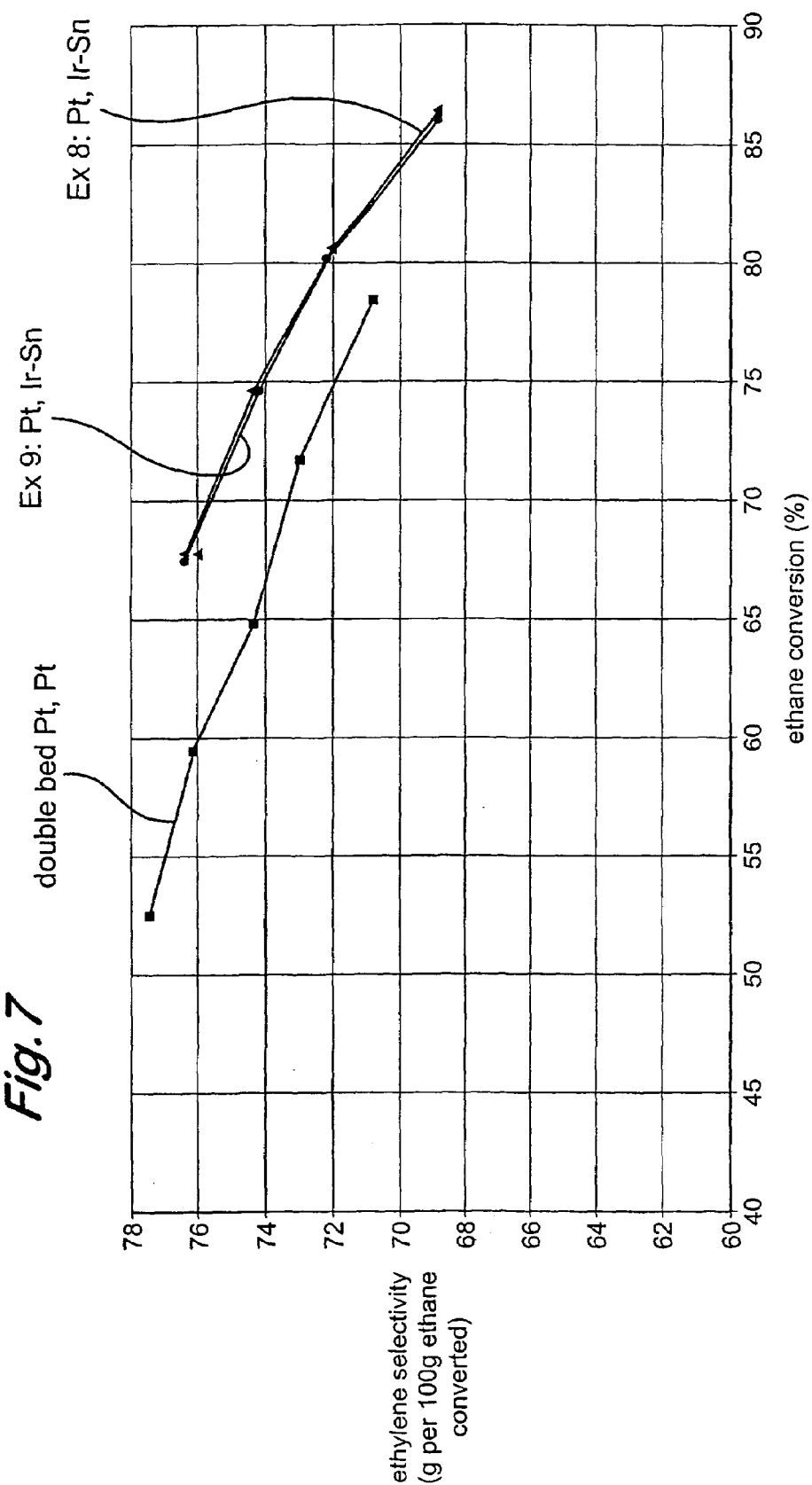
FIG. 7 is a graph showing the effect on ethylene selectivity of using double beds of Pt and Sn promoted Ir catalysts compared to a double bed of Pt-only catalyst.

Oxygen, ethane, hydrogen and nitrogen were then passed over the catalyst as described for Experiment 1. The corresponding changes in ethylene selectivity were measured and the results are shown in FIG. 7. Also shown on FIG. 7 are the ethylene selectivities obtained using a catalyst zone comprising two 3 wt % Pt catalyst beds (catalyst C). It can be seen that the olefin selectivities obtained using a catalyst zone comprising a bed of tin-promoted iridium catalyst positioned downstream of a platinum-only catalyst bed are superior to a catalyst zone comprising two beds of platinum-only catalyst.

Example 9 (Double Bed—3 wt % Pt on Alumina; 1 wt % Ir, 4 wt % Sn on Alumina)

Example 8 was repeated under identical process conditions. As can be seen from FIG. 7, the ethylene selectivities achieved are substantially the same as those obtained in Example 8.

Experiment 6 (Single Bed—3 wt % Pt on Alumina)

A bed of catalyst J having dimensions 15 mm diameter by 60 mm depth, and a volume of 10.60 cm$^3$ was loaded into the reactor of FIG. 1.

The catalyst bed was heated to approximately 200° C. under nitrogen at reaction pressure. The oxygen, ethane, hydrogen and nitrogen feeds were mixed and preheated to approximately 175° C. and then contacted with the catalyst under the conditions shown in Table 1 below. The reaction pressure was 1 bara.

From analysis of the feed and product flow rates and compositions, the ethane conversion and ethylene selectivity were calculated using the following equations:—

$$\text{Ethane conversion (\%)} = 100 * \frac{\text{Ethane in feed (g/min)} - \text{ethane in product (g/min)}}{\text{Ethane in feed (g/min)}}$$

$$\frac{\text{Ethylene selectivity}}{\text{(g per 100 g ethane converted)}} = 100 * \frac{\text{Ethylene in product (g/min)}}{\text{Ethane in feed (g/min)} - \text{ethane in product (g/min)}}$$

The results are given in Table 1.

Example 10 (Double Bed—3 wt % Pt on Alumina; 1 wt % Cu on Alumina)

Experiment 6 was repeated except that the reactor was loaded with a bed of catalyst K positioned immediately downstream of catalyst J such that there was no gap between the beds. The bed of catalyst K was of dimensions 15 mm diameter by 60 mm in depth.

The ethylene selectivities obtained in Example 10 are given in Table 1.

The catalyst bed was purged under nitrogen at 1.8 bara and the inlet gas temperature was raised to approximately 200° C. using electrical heaters.

The ethane, hydrogen, oxygen and nitrogen flows were mixed then passed over the catalyst bed with compositions as shown in Table 2.

The product composition was analysed by gas chromatography fitted with thermal conductivity and flame ionization detectors. Gas feed rates were controlled by thermal mass flow controllers (ex Bronkhorst HiTec BV)

TABLE 1

| Catalyst Zone | Pre-heat temp (° C.) | Catalyst face temp (° C.) | Catalyst exit temp (° C.) | $C_2H_6$ nl/min | $H_2$ nl/min | $O_2$ nl/min | feed $N_2$ nl/min | total feed to reactor | $O_2/C_2H_6$ feed ratio (wt/wt) | ethane conversion (%) | $C_2H_4$ selectivity per 100 g ethane converted |
|---|---|---|---|---|---|---|---|---|---|---|---|
| Expt 6 | 180 | 491 | 912 | 6.46 | 6.30 | 3.15 | 1.77 | 17.68 | 0.65 | 63.30 | 71.66 |
| Expt 6 | 180 | 500 | 924 | 6.18 | 6.49 | 3.24 | 1.78 | 17.69 | 0.70 | 69.98 | 69.83 |
| Expt 6 | 178 | 507 | 933 | 5.92 | 6.66 | 3.33 | 1.76 | 17.67 | 0.75 | 76.30 | 67.92 |
| Expt 6 | 176 | 514 | 945 | 5.68 | 6.82 | 3.41 | 1.74 | 17.65 | 0.80 | 81.77 | 65.35 |
| Ex 10 | 182 | 621 | 911 | 7.48 | 5.61 | 2.81 | 1.56 | 17.46 | 0.50 | 47.43 | 79.07 |
| Ex 10 | 181 | 635 | 919 | 7.11 | 5.86 | 2.93 | 1.55 | 17.45 | 0.55 | 53.46 | 78.18 |
| Ex 10 | 181 | 652 | 928 | 6.77 | 6.06 | 3.05 | 1.53 | 17.41 | 0.60 | 60.67 | 76.35 |
| Ex 10 | 175 | 662 | 933 | 6.46 | 6.30 | 3.15 | 1.54 | 17.45 | 0.65 | 67.04 | 74.79 |
| Ex 10 | 178 | 680 | 941 | 6.18 | 6.49 | 3.24 | 1.52 | 17.43 | 0.70 | 73.25 | 72.60 |
| Ex 10 | 179 | 694 | 950 | 5.92 | 6.66 | 3.33 | 1.52 | 17.43 | 0.75 | 78.50 | 70.70 |
| Ex 10 | 177 | 717 | 968 | 5.68 | 6.82 | 3.41 | 1.54 | 17.45 | 0.80 | 85.03 | 67.05 |

As can be seen from Table 1 the use of a catalyst zone comprising a bed of copper-only catalyst placed downstream of a platinum-only catalyst bed shows superior olefin selectivity compared to a catalyst zone comprising a single bed of platinum-only catalyst.

Experiment 7 (Single Bed—3 wt % Pt on Alumina Spheres)

Catalyst L was tested as a packed bed of spheres supported on an alumina foam block of dimensions 15 mm diameter, 10 mm depth and of porosity 30 pores per inch. The catalyst bed was of dimensions 15 mm diameter and 60 mm deep and of volume 10.60 cm³. A bed of the catalyst was placed in a metallic reactor (internal diameter 15 mm) with a quartz lining and fitted with a pressure jacket. The pressure jacket was not externally heated.

From analysis of the feed and product flow rates and compositions, the ethane conversion and ethylene selectivities were calculated using equations as given under Experiment 6 above and the results are shown in Table 2.

Example 11 (Double Bed—3 wt % Pt on Alumina Spheres; 1 wt % Cu on Alumina Spheres)

The procedure as for Experiment 7 was repeated except that a double catalyst bed was used. A bed of catalyst M (15 mm diameter; 30 mm deep) was placed immediately downstream of a bed of catalyst L (15 mm diameter; 30 mm deep) such that there was no gap between the two beds. Catalyst bed M was supported on an alumina foam block of dimensions 15 mm diameter, 10 mm depth and of porosity 30 pores per inch.

The ethylene selectivities achieved are given in Table 2.

TABLE 2

| Catalyst | feed temp (° C.) | Catalyst face temp (° C.) | Catalyst exit temp (° C.) | $C_2H_6$ nl/min | H2 nl/min | $O_2$ nl/min | $N_2$ nl/min | total to reactor nl/min | $O_2/C_2H_6$ feed ratio (wt/wt) | $C_2H_6$ conv (%) | $C_2H_4$ g per 100 g ethane converted |
|---|---|---|---|---|---|---|---|---|---|---|---|
| L | 247 | 744 | 816 | 41.64 | 31.04 | 15.61 | 3.10 | 91.39 | 0.50 | 37.11 | 68.80 |
| L | 249 | 754 | 836 | 39.45 | 32.61 | 16.29 | 3.08 | 91.44 | 0.55 | 44.67 | 67.16 |
| L | 246 | 764 | 852 | 37.56 | 33.85 | 16.93 | 0.00 | 88.33 | 0.60 | 50.11 | 68.07 |
| L | 246 | 775 | 865 | 35.89 | 34.85 | 17.48 | 3.04 | 91.26 | 0.65 | 55.56 | 66.23 |
| L | 245 | 774 | 875 | 34.30 | 35.97 | 18.01 | 3.06 | 91.34 | 0.70 | 62.74 | 66.12 |
| L | 245 | 778 | 885 | 32.89 | 36.87 | 18.49 | 3.12 | 91.37 | 0.75 | 68.41 | 63.28 |
| L | 244 | 781 | 895 | 31.57 | 37.88 | 18.96 | 3.08 | 91.50 | 0.80 | 73.80 | 63.09 |
| L | 244 | 779 | 907 | 30.31 | 38.66 | 19.33 | 3.08 | 91.39 | 0.85 | 78.89 | 60.95 |
| L and M | 240 | 950 | 920 | 41.62 | 31.16 | 15.61 | 4.42 | 92.80 | 0.50 | 56.66 | 76.68 |
| L and M | 241 | 905 | 931 | 39.47 | 32.61 | 16.31 | 4.32 | 92.72 | 0.55 | 63.45 | 75.55 |
| L and M | 241 | 861 | 941 | 37.60 | 33.85 | 16.94 | 4.15 | 92.53 | 0.60 | 70.20 | 72.17 |
| L and M | 241 | 848 | 951 | 35.90 | 34.97 | 17.47 | 4.07 | 92.40 | 0.65 | 74.95 | 71.84 |
| L and M | 242 | 851 | 963 | 34.32 | 35.97 | 18.01 | 3.99 | 92.29 | 0.70 | 80.62 | 67.67 |
| L and M | 242 | 860 | 975 | 32.90 | 36.98 | 18.51 | 3.92 | 92.31 | 0.75 | 84.74 | 66.23 |

TABLE 2-continued

| Catalyst | feed temp (° C.) | Catalyst face temp (° C.) | Catalyst exit temp (° C.) | $C_2H_6$ nl/min | H2 nl/min | $O_2$ nl/min | $N_2$ nl/min | total to reactor nl/min | $O_2/C_2H_6$ feed ratio (wt/wt) | $C_2H_6$ conv (%) | $C_2H_4$ g per 100 g ethane converted |
|---|---|---|---|---|---|---|---|---|---|---|---|
| L and M | 242 | 873 | 989 | 31.57 | 37.88 | 18.95 | 3.86 | 92.26 | 0.80 | 88.58 | 63.00 |
| L and M | 242 | 887 | 1006 | 30.32 | 38.66 | 19.33 | 3.80 | 92.11 | 0.85 | 91.82 | 59.19 |

Catalyst L = 3 wt % Pt on alumina
Catalyst M = 1 wt % Cu on alumina

Table 2 clearly demonstrates that a catalyst zone comprising a bed of copper catalyst placed downstream of a platinum-only catalyst achieves greater olefin selectivity compared to a catalyst zone comprising a single bed of platinum catalyst.

The invention claimed is:

1. A process for the production of an olefin from a hydrocarbon, said process comprising passing a mixture of said hydrocarbon and an oxygen-containing gas through a catalyst zone to produce said olefin, said catalyst zone comprising at least a first catalyst bed and a second catalyst bed, wherein the first catalyst bed comprises a catalyst which is capable of supporting combustion beyond the fuel rich limit of flammability, wherein the second catalyst bed is located downstream of the first catalyst bed, is of a different composition to the first catalyst bed and comprises at least one metal selected from the group consisting of Mo, W, and Groups IB, IIB, IIIB, IVB, VB, VIIB and VIII of the Periodic Table, and wherein the second catalyst bed comprises either:
   (i) a catalyst which is substantially incapable of supporting combustion beyond the fuel rich limit of flammability and which is a dehydrogenation catalyst, or
   (ii) a catalyst which is a promoted Group VIII metal catalyst,
   and wherein the molar ratio of said hydrocarbon to the oxygen-containing gas is 5 to 16 times the stoichiometric ratio of hydrocarbon to oxygen-containing gas required for complete combustion to carbon dioxide and water.

2. A process according to claim 1 wherein the first catalyst bed comprises a Group VIII metal.

3. A process according to claim 1 wherein the first catalyst bed comprises a Group VIII metal selected from the group consisting of rhodium, platinum, palladium and mixtures thereof.

4. A process according to claim 1 wherein the first catalyst bed comprises platinum.

5. A process according to claim 1 wherein the first catalyst bed comprises a promoted catalyst.

6. A process according to claim 1 wherein the promoter is selected from the group consisting of transition metals and Groups IIIA, IVA and VA of the Periodic Table and mixtures thereof with the proviso that where the promoter is a transition metal, the transition metal used as the promoter is different to the transition metal used as the catalyst.

7. A process according to claim 6 wherein the promoter is selected from the group consisting of copper and tin.

8. A process according to claim 1 wherein the first catalyst bed is selected from the group consisting of Pt/Ga, Pt/In, Pt/Ge, Pt/Cu, Pt/Sn, Pd/Ge, Pd/Sn, Pd/Cu and Rh/Sn.

9. A process according to claim 1 wherein the dehydrogenation catalyst comprises a metal selected from the group consisting of Cu, Ag, Au, Zn, Cd, Hg, Sc, Y, La, Ti, Zr, Hf, V, Nb, Ta, Ni, Co, Ir and mixtures thereof.

10. A process according to claim 1 wherein the dehydrogenation catalyst is promoted with at least one promoter selected from the group consisting of Group IVA of the Periodic Table and the transition metals.

11. A process according to claim 10 wherein the promoter is selected from the group consisting of Sn, Cr and Cu.

12. A process according to claim 1 wherein the second catalyst bed is selected from the group consisting of Ni/Sn, Co/Sn, Co/Cu, Cu/Cr, Ir/Sn, Fe/Sn, Ru/Sn, Ni/Cu, Cr/Cu, Ir/Cu, Fe/Cu, Ru/Cu and Cu.

13. A process according to claim 1 wherein the Group VIII metal of the second catalyst bed is selected from the group consisting of rhodium, platinum, palladium and mixtures thereof.

14. A process according to claim 13 wherein the Group VIII metal of the second catalyst bed is promoted with at least one promoter selected from the group consisting of the transition metals and Groups IIIA, IVA and VA of the Periodic Table and mixtures thereof with the proviso that where the promoter is a transition metal, the transition metal used as the promoter is different to the Group VIII metal(s) used as the catalyst.

15. A process according to claim 14 wherein the promoter is selected from the group consisting of Sn, Cr, Mo, W, Fe, Ru, Os, Co, Rh, Ir, Ni, Pt, Cu, Ag, Au, Zn, Cd and Hg.

16. A process according to claim 1 wherein the second catalyst bed is selected from the group consisting of Pt/Ga, Pt/In, Pt/Ge, Pt/Cu, Pt/Sn, Pd/Ge, Pd/Sn, Pd/Cu and Rh/Sn.

17. A process for the production of an olefin from a hydrocarbon, said process comprising passing a mixture of said hydrocarbon and an oxygen-containing gas through a catalyst zone to produce said olefin, said catalyst zone comprising at least a first catalyst bed and a second catalyst bed, wherein the first catalyst bed comprises a Group VIII metal catalyst, said catalyst being a mixture of at least two of rhodium, platinum and palladium and/or being a promoted Group VIII metal catalyst, and wherein the second catalyst bed is located downstream of the first catalyst bed, is of a different composition to the first catalyst bed and comprises a Group VIII metal, and wherein the molar ratio of hydrocarbon to the oxygen-containing gas is 5 to 16 times the stoichiometric ratio of hydrocarbon to oxygen-containing gas required for complete combustion to carbon dioxide and water.

18. A process according to claim 17 wherein the first catalyst bed comprises platinum.

19. A process according to claim 17 wherein the first catalyst bed comprises platinum and palladium.

20. A process according to claim 1 or claim 17 wherein the Group VIII metal of the second catalyst bed is selected from the group consisting of rhodium, platinum, palladium and mixtures thereof.

21. A process according to claim 1 or claim 17 wherein the first catalyst bed and/or the second catalyst bed is supported.

22. A process according to claim 21 wherein the support is a ceramic support.

23. A process according to claim 1 or claim 17 wherein the catalyst zone further comprises additional catalyst beds, the catalyst used for the additional beds being the same as that of the second catalyst bed.

24. A process according to claim 23 wherein the catalyst zone comprises 3 to 10 beds.

25. A process according to claim 1 or claim 17 wherein the first and second catalyst beds are directly adjacent to one another.

26. A process according to claim 1 or claim 17 wherein a space is provided between the first and second catalyst beds.

27. A process according to claim 1 or claim 17 wherein the hydrocarbon is a paraffin-containing hydrocarbon feed having at least two carbon atoms.

28. A process according to claim 27 in which the hydrocarbon is selected from the group consisting of ethane, propane, butane, naphtha, gas oil, vacuum gas oil and mixtures thereof.

29. A process according to claim 1 or claim 17 in which hydrogen is a co-feed.

30. A process according to claim 29 in which the molar ratio of hydrogen to oxygen-containing gas is in the range 0.2 to 4.

31. A process according to claim 1 or claim 17 wherein the process is conducted at a gas hourly space velocity of greater than 10,000/h.

* * * * *